United States Patent [19]
Pfleiderer et al.

[11] Patent Number: 6,153,744
[45] Date of Patent: Nov. 28, 2000

[54] NUCLEOSIDE DERIVATIVES WITH PHOTOLABILE PROTECTIVE GROUPS

[75] Inventors: Wolfgang Pfleiderer; Sigrid Bühler, both of Constance, Germany

[73] Assignee: Wolfgang Pfleiderer, Constance, Germany

[21] Appl. No.: 09/193,087

[22] Filed: Nov. 16, 1998

Related U.S. Application Data

[63] Continuation of application No. PCT/EP97/02257, May 2, 1997.

[30] Foreign Application Priority Data

May 20, 1996 [DE] Germany .............. 196 20 170

[51] Int. Cl.[7] ............. C07H 19/052; C07H 19/067; C07H 19/167; C07H 21/00
[52] U.S. Cl. .............. 536/25.3; 536/25.31; 536/25.33; 536/25.34; 536/27.6; 536/27.61; 536/27.8; 536/27.81; 536/28.5; 536/28.52; 536/28.53; 536/28.8
[58] Field of Search ............. 536/25.3, 25.31, 536/25.33, 25.34, 27.6, 27.61, 27.8, 27.81, 28.5, 28.52, 28.53, 28.8

[56] References Cited

FOREIGN PATENT DOCUMENTS

| | | |
|---|---|---|
| 3606394 | 9/1987 | Germany . |
| 3606395 | 9/1987 | Germany . |
| WO 96/18634 | 6/1996 | WIPO . |

OTHER PUBLICATIONS

Giegrich et al., "New Photo–Labile Protecting Groups in Nucleoside and Nucleotide Chemistry—Synthesis,Cleavage Mechanisms and Applications," *Nucleosides & Nucleotides*, 17(9–11), 19897–1996 (1998); only abstract supplied.

Pfleiderer et al., "New Protecting Groups in Nucleotide Chemistry," in *Biophosphates and Their Analogues–Synthesis, Structure, Metabolism and Activity*, pp. 133–142, XP000570661. (Sep. 8, 1986).

Schirmeister et al., "21. Nucleosides," *Helvetica Chimica ACTA*, vol. 76, No. 1, 1993, pp. 385–401.

Uhlmann et al., "New Improvements in Oligonucleotide Synthesis by Use of the p–Nitrophenylethyl Phosphate Blocking Group and its Deprotection by DBU on DBN," *Tetrahedron Letters*, vol. 21, pp. 1181–1184, 1980, XP002041323.

*Primary Examiner*—Gary Geist
*Assistant Examiner*—L. Eric Crane
*Attorney, Agent, or Firm*—Fitch, Even, Tabin & Flannery

[57] ABSTRACT

The invention relates to nucleo-side derivatives with photo-unstable protective groups of the general formula (I)

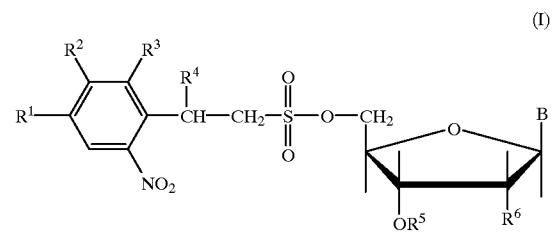

in which $R^1$ is H, $NO_2$, CN, $OCH_3$, halogen, alkyl or alkoxyalkyl with 1 to 4 C atoms, $R^2$ is H, $OCH_3$, $R^3$ is H, F, Cl, Br, $NO_2$ or an aliphatic acyl radical with 2 to 5 C atoms, $R^4$ is H, halogen, $OCH_3$, an alkyl radical with 1 to 4 C atoms or a possibly substituted aryl radical, $R^5$ is H or a conventional functional group for producing oligonucleotides, $R^6$ is H, OH, halogen or $XR^8$, where X is O or S and $R^8$ is a conventional protective group in nucleotide chemistry, B is adenine, cytosin, guanine, thymine, uracil, 2,6-diaminopurin-9-yl, hypoxanthin-9-yl, 5-methylcytosin-1-yl, 5-amino-4-imidazol carboxylic acid amid-1-yl or 5-amino-4-imidazol carboxylic acid amide-3-yl, where, if B is adenine, cytosin or guanine, the primary amino function may have a permanent protective group. These derivatives may be used for the light-controlled synthesis of oligonucleotides on a DNA chip.

31 Claims, No Drawings

NUCLEOSIDE DERIVATIVES WITH PHOTOLABILE PROTECTIVE GROUPS

This is a continuation, of prior application Ser. No. PCT/EP97/02257, filed May 2, 1997, designating the U.S., which is hereby incorporated herein by reference in its entirety.

DESCRIPTION

Subject matter of the present invention relates to nucleoside derivatives with photolabile protective groups and a method for their preparation.

Photolabile protective groups for the hydroxy and phosphate functions in nucleosides and nucleotides are of particular interest since they are suitable for example for light-controlled parallel syntheses of oligonucleotides on a solid carrier (cf. S. P. A. Fodor et al. Science 1991, 251, p. 767 et seq.). They enable the production of so-called DNA chips (i.e. carrier plates on the surface of which a great number of many different oligonucleotides are arranged), which in turn are required in molecular biology for a rapid DNA sequence analysis.

In the prior art, the o-nitrobenzyl group and its derivatives have so far mainly been used as photolabile protective groups in nucleoside and nucleotide chemistry (cf. V. N. R. Pillai, Org. Photochem. 1987, 9, p. 225 et seq. and J. W. Walker et al., J. Am. Chem. Soc. 1988, 110, p. 7170 et seq.). The slow and partially only incomplete deprotection of the corresponding nucleoside and nucleotide derivatives proved to be a particular disadvantage of these protective groups. Furthermore, undesirable by-products in the form of toxic nitrosophenyl compounds are also obtained to some extent during the cleavage of the o-nitrobenzyl compounds.

According to the article by W. Pfleiderer et al. in "Biophosphates and Their Analogues—Synthesis, Structure, Metabolism and Activity", Elsevier Science Publishers B. V. (Amsterdam) 1987, p. 133 et seq., the 2-(o-nitrophenyl)ethyl group which however is introduced solely as a protective group in the base part, particularly in $O^6$ position of a guanosine, was also recommended as another photolabile protective group for nucleosides. The same publication also describes the p-nitrophenylethoxycarbonyl (NPEOC) and the 2,4-dinitrophenylethoxycarbonyl (DNPEOC) groups both as protective groups for the amino function and for the hydroxyl functions in the sugar part, though elimination of these groups has been carried out solely by means of base-catalyzed β-elimination.

The present invention therefore has as its object to develop nucleoside derivatives with photolabile protective groups for the 5'-OH function in the sugar part, which derivatives do not exhibit the named disadvantages of the prior art, but can be deprotected comparatively quickly, quantitatively and without the formation of undesirable by-products.

This object was solved according to the invention by means of nucleoside derivatives of the general formula (I) according to claim 1. Surprisingly, it was in fact shown that the protective groups according to the invention can be eliminated much more quickly and completely than for example the o-nitrobenzyl groups. It has so far not been possible to find any undesirable by-products to a large extent during deprotection, which had not been predictable either.

The nucleoside derivatives according to the invention have the following general formula (I):

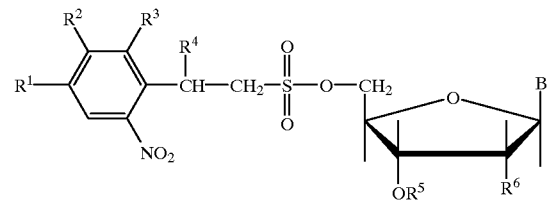

wherein the radicals $R^1$, $R^2$ and $R^3$ at the phenyl ring may have the following meaning:

$R^1$=H, $NO_2$, CN, $OCH_3$, halogen or alkyl or alkoxyalkyl with 1 to 4 C atoms $R^2$=H, $OCH_3$ $R^3$=H, F, Cl, Br, $NO_2$ or an aliphatic acyl radical with 2 to 5 C-atoms (such as acetyl for example).

The radical $R^4$ located on the $C_2$ atom of the o-nitrophenylethyl group may be either H, halogen, $OCH_3$, an alkyl radical with 1 to 4 C atoms or an optionally substituted aryl radical. The alkyl radical may in this regard be linear or branched, substituted (particularly with one or more halogen atoms) or unsubstituted as well as saturated or unsaturated; the same also applies to the alkyl and alkoxyalkyl radicals in $R^1$. $R^4$ preferably represents a methyl radical. The aryl radical preferably represents a phenyl group which can be optionally further substituted with alkyl (with 1 to 4 C-atoms), alkoxy (for example methoxy) or dialkylamino groups (for example dimethylamino) and/or F, Cl, Br, $NO_2$ or CN. In the event that $R^4 \neq H$, the substituents $R^1$, $R^2$ and $R^3$ at the phenyl ring are preferably hydrogen radicals.

In this application, halogen consistently means F, Cl, Br, I and preferably F, Cl or Br.

The nucleoside part of the compounds according to the invention is composed of the usual D-ribofuranose or 2'-deoxyribofuranose units and the pyrimidine (B=cytosine, thymine, uracil) or purine bases (B=adenine, guanine). 2,6-diaminopurin-9-yl, hypoxanthin-9-yl, 5-methylcytosin-1-yl, 5-amino-4-imidazolcarboxamid-1-yl or 5-amino-4-imidazolcarboxamid-3-yl radicals can also be used as bases.

The OH group(s) in the ribofuranoside or 2'-deoxyribofuranose part may be free or protected, depending on demand. In this regard, the known phosphoramidite groups such as

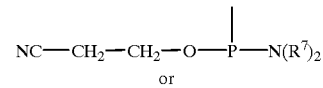

or

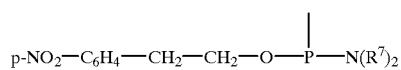

have been successful in protecting the 3' position, whereby the $R^7$ groups can be the same or different and mean linear or branched alkyl radicals with 1 to 4 C atoms. They are preferably ethyl or isopropyl radicals.

In the 2' position of the ribofuranoside part (position $R^6$) a free or a protected OH group may be present as well as a hydrogen or halogen atom (particularly F, Cl, Br), whereby any protective group ($R^8$) common in nucleotide chemistry may be used. It is possible to employ the conventional alkyl, alkenyl, acetal or silyl ether protective groups for oxygen atoms (X=O). $R^6$ may also represent an S-alkyl group (X=S, $R^8$=alkyl). Preferred examples for O-alkyl protective groups. are O-methyl or O-ethyl radicals; for O-alkenyl protective groups, O-allyl radicals; for O-acetal protective groups, O-tetrahydropyranyl or O-methoxytetrahydropyranyl radicals; and for O-silyl ether protective groups, O-t-butyldimethylsilyl radicals.

According to a preferred embodiment, the pyrimidine or purine bases with primary amino functions (e.g. adenine, cytosine and guanine) may also contain preferably carbonyl-based permanent protective groups. In this respect, phenoxy-acetyl or dimethylformamidino radicals are preferred which are possible for all three designated bases. There are also special protective groups which are introduced only in the case of certain bases. In the case of adenine, for example, these are benzoyl or p-nitrophenyl ethoxycarbonyl (p-NPEOC) radicals. In addition to the p-NPEOC radicals, isobutyroyl or p-nitrophenylethyl (p-NPE) protective groups can also be introduced for guanine. Finally, as well as the p-NPEOC radicals, benzoyl protective groups are suitable for cytosine.

The preparation of the nucleoside derivatives according to the invention can be conducted in three steps. In the first step a), an alcohol of the general formula (II)

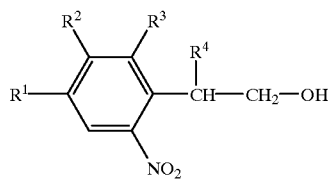

in which $R^1$, $R^2$, $R^3$ and $R^4$ have the above-identified meaning, is reacted with thionyl chloride, preferably in a nonpolar organic solvent at temperatures between 50 and 120° C., optimally in the presence of a base.

The alcohol component is known in most cases or can be analogously produced according to known processes. In step a), toluene is preferably used as a nonpolar organic solvent and pyridine is preferably used as a base in an amount of 2 to 10% by volume with respect to the toluene used. Although the reaction components can be reacted in an approximately stoichiometric ratio, thionyl chloride is preferably used in a clear excess, for example in a two- to five-fold molar excess, in relation to the alcohol component. The alcohol component concentration can also be varied within broad limits though it has proved particularly advantageous to set this concentration to 1.0 to 20.0 mmol per 10 ml solvent.

The corresponding phenylalkyl chlorides of the general formula (III)

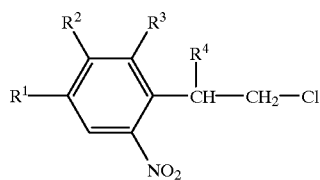

are obtained in this reaction (reaction duration approx. 1 to 3 hours) with a good purity and in a high yield (>85%).

Processing of the corresponding products preferably occurs by first treating the reaction solution with ice water, and optionally several times with chloroform or dichloromethane, neutralizing the organic phases (for example with bicarbonate), optionally drying, removing the solvent and subsequently purifying the corresponding product, optionally by distillation of crystallization.

In the subsequent reaction step b), the phenylalkyl chlorides of the general formula (III) are first reacted with sodium thiosulfate to the corresponding esters and then with chlorine to a phenylalkylsulfonyl chloride of the general formula (IV)

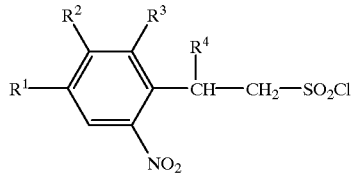

The reaction with sodium thiosulfate preferably occurs in a solvent mixture consisting of an alcohol and water at temperatures between 50 and 100° C., wherein a concentration ratio of 10 to 100 mmol phenylalkyl chloride is particularly set per 10 ml alcohol/water mixture. Above all, methanol and ethanol have proven themselves best as alcohols. The mass ratio of alcohol to water can be varied over a broad range, but it has been proven to be advantageous to adjust the ratio of alcohol to water to approximately 1:1.

The mass ratio of phenylalkyl chloride to sodium thiosulfate should be at least 1:1 but, according to a preferred embodiment, work is done with a clear excess of sodium thiosulfate which is particularly 1.5 to 2.5 mmol per mmol phenylalkyl chloride. After finishing the reaction, which is ended as a rule after 10 to 20 hours, the solvent is entirely or considerably removed according to customary methods and the corresponding esters are reacted, without further isolation or processing, with chlorine to the corresponding phenylalkylsulfonyl chlorides. This chlorination is preferably carried out in water, a water/acetic acid mixture (preferred mass ratio 4:1 to 2:1) or a water/dichloromethane mixture (preferred mass ratio 2:1 to 1:1) at temperatures between 0 and 10° C., wherein work can be done with a large excess of chlorine. Preferably, work is carried out in this step at a concentration of 5 to 30 mmol phenylalkyl chloride per 100 ml solvent.

After the chlorine treatment (approximately 10 to 30 minutes), the precipitate is separated and the crude product is purified according to known methods such as crystallization or column chromatography, wherein the corresponding phenylalkylsulfonyl chlorides accumulate in very different yields as either solids or in the form of oils.

The phenylalkylsulfonyl chlorides are finally reacted in reaction step c) with the nucleosides of the general formula (V)

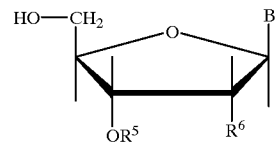

wherein $R^5$, $R^6$ and B have the above meaning.

The reaction is preferably carried out in a solvent mixture consisting of dichloromethane and pyridine temperatures between −60 and 0° C. The mixture ratio of dichloromethane to pyridine is relatively uncritical, although 1 to 3 parts by volume dichloromethane per part by volume pyridine are preferably used.

According to a preferred embodiment, the corresponding nucleoside (V) dissolved in pyridine is charged and a solution of the phenylalkylsulfonyl chloride in dichloromethane is added drop-wise at the respective reaction temperature. The molar ratio of nucleoside to phenylalkylsulfonyl chloride can be adjusted according to the stoichiometry to approx. 1:1. Nevertheless, an excess of phenylalkylsulfonyl chloride is preferably used, this amount being such that the molar ratio of nucleoside to phenylalkylsulfonyl chloride is 1:1 to 1:2. Finally, the concentration of the nucleoside in the solvent mixture can also be varied within broad limits, though it is preferably set to 0.1 to 3.0 mmol per 10 ml solvent.

Once the reaction has been completed (reaction time approx. 1 to 10 hours), the nucleoside derivatives according to the invention can be isolated or purified according to known methods, such as dilution with dichloromethane, removing any salts by washing with water, drying of the organic phase, concentration of the solution or crystallization and subsequent column chromatography. The corresponding nucleoside derivatives can be obtained in this manner with a high purity and in good yields (30 to 65%).

According to a preferred embodiment and following on from reaction step b), the phosphoramidite group

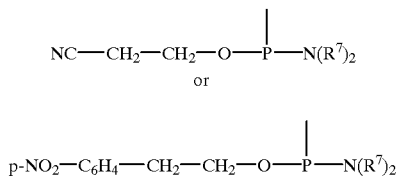

can be introduced into the 3' position of the nucleoside derivatives with $R^5$=H according to known methods. This reaction with the corresponding phosphines usually takes place in the presence of 1H tetrazole as an activator in a solvent mixture composed of dichloromethane and acetonitrile at temperatures between 0 and 25° C. The phosphine is preferably used in a two- to three-fold molar excess whereas the molar ratio of phosphine to 1H tetrazole is set to 3: approx. 1.0. The quantitative ratio of dichloromethane to acetonitrile is not very critical and is preferably 1:1 to 4:1. After the reaction has taken place (approx. 10 to 20 h), the corresponding nucleoside can be worked up as described in step c).

As irradiation experiments with polychromatic light having a wavelength of >289 nm prove, the nucleosides according to the invention can be deprotected very quickly ($t_{0.5}$=1 to 40 min) and extensively (yields of up to 97%), thus satisfying the special requirements expected of the protective group's photolability to an excellent degree.

On account of these special properties, the nucleosides according to the invention are extremely suitable for the preparation of oligonucleotides by cleaving the protective groups in a light-controlled manner, particularly on solid carrier plates.

The following examples are intended to illustrate the invention in greater detail.

EXAMPLES

Solvents and Reagents

Solvents were distilled or dried according to customary methods. Only distilled solvents were used for chromatography. All chemicals used for the syntheses were employed at p.a. quality.

Chromatography

Analytical thin layer chromatography was carried out on finished films of the company Merck with fluorescence label (silica gel 60, $F_{254}$). Flash silica gel from Baker was used for preparative flash chromatography. Work was carried out at a positive pressure between 0.25 to 0.35 bar.

UV/VIS Absorption Spectra

The UV-Spectra were measured in methanol (Uvasol, Merck) with a spectrometer from Perkin-Elmer, Model Lambda 5. In the synthesis instructions λ [nm] and (1 g ε) are each provided. Shoulders were placed in [0] brackets.

$^1$H-NMR Spectra

A 250 MHz-FT-Spectrometer, Model AC 250, from Bruker served to take $^1$H-NMR-spectra. The Spectra were calibrated to the proton signals of the solvent ($CDCl_3$: 7.24, $D_6$-DMSO: 2.49).

Abbreviations
Sol.=solvent
EE=acetic acid ethyl ester
PE=petroleum ether
TOL=toluene
NPE=2-(4-nitrophenyl)ethyl-)
NPES=2-(2-nitrophenyl)ethylsulfonyl-)
NPPS=2-(2-nitrophenyl)propylsulfonyl-)

Production of the Phenylalkyl Chlorides

Example 1

2-(2-nitrophenyl)ethyl chloride 2.1 ml abs. pyridine and 21.62 g thionyl chloride (13.3 ml,. 0.18 mol) is added to 10.13 9 2-(2-nitrophenyl)ethanol (60 mmol) in 36 ml abs. toluene. After 2 h reflux, this is cooled and poured onto ice. The ice water is mixed with 50 ml chloroform and extracted 2× each with 50 ml chloroform. The combined organic phases are neutralized 2× each with 100 ml saturated bicarbonate solution. After drying with $Na_2SO_4$, this is filtered and rotary evaporated. After distillation under high-vacuum, 9.7 9 (50 mmol,. 87%) 2-(2-nitrophenyl)ethyl chloride is obtained as a yellow oil with a boiling point of 66 to 67° C. (0.001 mbar).

TLC (silica gel): $R_f$=0.39 (PE/EE 9:1); $^1$H-NMR (250 MHz, $CDCl_3$): 8.00 (dd, 1H, arom. H, o to $NO_2$), 7.59 (t, 1H, arom. H), 7.45 (m, 2H, arom. H), 3.85 (t, 2H, α-$CH_2$), 3.38 (t, 2H, β-$CH_2$); UV (MeOH), λ [nm] (1 g ε): 204 (4.06), [216 (3.78)], 256 (3.69).

Example 2

2-(2-chloro-6-nitrophenyl)ethyl chloride 15.60 9 g thionyl chloride (130 mmol) in 10 ml toluene (abs.) is added quickly in a drop-wise manner to 8.8 g 2-(2-chloro-6-nitrophenyl) ethanol (44 mmol) in 100 ml abs. toluene. The reaction solution is heated under reflux 1 h. After cooling, this is poured onto ice, diluted with 50 ml $CH_2Cl_2$ and the $H_2O$ phase is extracted 2× each with 50 ml $CH_2Cl_2$. The combined organic phases are dried over $Na_2SO_4$ and rotary evaporated. 9.08 g (41 mmol, 94%) 2-(2-chloro-6-nitrophenyl)ethyl chloride are obtained as a brown oil which crystallizes after storage for several days in a refrigerator.

TLC (silica gel): $R_f$=0.71 (PE/EE 7:3); MP.: <25° C.; 1H-NMR (250 MHz, $CDCl_3$): 7.76 (dd, 1H, arom. H), 7.66 (dd, 1H, arom. H), 7.38 (t, 1H, arom. H, m to $NO_2$), 3.80 (m, 2H, α-$CH_2$), 3.44 (m, 2H, β-$CH_2$); UV (MeOH), λ [nm] (1 g ε): 212 (3.78), 252 (3.55), [286 (3.15)]; Elemental analysis: $C_8H_7Cl_2NO_2$ (220.1 g/mol)

|       | C     | H    | N    |
|-------|-------|------|------|
| calc. | 43.66 | 3.21 | 6.36 |
| found | 43.95 | 3.35 | 6.31 |

Example 3

2-(4-chloro-2-nitrophenyl)ethyl chloride 12 g thionyl chloride (7.4 ml, 100 mmol) in 10 ml toluene (abs.) are quickly added in a drop-wise manner to a solution of 6.78 g 2-(4-chloro-2-nitrophenyl)ethanol (33 mmol) in 100 ml abs. toluene and 2.5 ml pyridine. This is heated 2 h under reflux, cooled, poured onto 100 g ice and mixed with 100 ml $CH_2Cl_2$. The aqueous phase is extracted 2× each with 50 ml $CH_2Cl_2$. The combined organic phases are neutralized 2× each with 80 ml saturated bicarbonate solution, dried over $Na_2SO_4$, filtered and rotary evaporated. 7.12 g (32 mmol, 98%) 2-(4-chloro-2-nitrophenyl)ethyl chloride are obtained as a brown oil which hardens to a brown solid after some days in the refrigerator.

TLC (silica gel): $R_f$=0.54 (PE/EE 9:1); MP.: <25° C.; $^1$H-NMR (250 MHz, $CDCl_3$): 8.01 (d, 1H, $H_a$), 7.57 (dd, 1H, $H_b$), 7.41 (d, 1H, $H_c$), 3.83 (t, 2H, α-$CH_2$), 3.35 (t, 2H, β-$CH_2$); UV (MeOH), λ [nm] (1 g ε): 214 (4.27), 254 (3.65), 293 (3.48); Elemental analysis: $C_8H_7Cl_2NO_2$ (220.1 g/mol)

|       | C     | H    | N    |
|-------|-------|------|------|
| calc. | 43.67 | 3.21 | 6.37 |
| found | 43.72 | 3.14 | 6.15 |

Example 4

2-(2,4-dinitrophenyl)ethyl chloride 20 g 2-(2,4-dinitrophenyl)ethanol (94 mmol) are dissolved in 120 ml abs. toluene and 4 ml pyridine. 34 g thidnyl chloride (21 ml, 282 mmol) in 20 ml abs. toluene are quickly added in a drop-wise manner. After 2 h under reflux, this is cooled and poured onto ice. This is mixed with 100 ml $CH_2Cl_2$ and the aqueous phase is extracted 2× each with 50 ml $CH_2Cl_2$. The combined organic phases are dried over $Na_2SO_4$, filtered and rotary evaporated. 21.51 g (93 mmol, 98%) 2-(2,4-dinitrophenyl)ethyl chloride are obtained as a brown oil.

TLC (silica gel): $R_f$=0.62 (PE/EE 7:3); $^1$H-NMR (250 MHz, $CDCl_3$): 8.87 (d, 1H, $H_a$), 8.44 (dd, 1H, $H_b$), 7.71 (d, 1H, $H_c$), 3.90 (t, 2H, α-$CH_2$), 3.50 (t, 2H, β-$CH_2$); UV (MeOH), λ [nm] (1 g ε): 211 (4.43), 266 (4.22), [273 (4.16)].

Example 5

2-(2-nitrophenyl)propyl chloride 12.16 g thionyl chloride (7.5 ml, 102 mmol) in 10 ml toluene (abs.) are added quickly in a drop-wise manner to 6.2 g 2-(2-nitrophenyl)propanol (34 mmol) in 90 ml abs. toluene and 2 ml pyridine. The reaction solution is heated 1 h under reflux. After cooling, this is poured onto 100 g ice and mixed with 80 ml $CH_2Cl_2$. The $H_2O$ phase is extracted 2× each with 80 ml $CH_2Cl_2$. The combined organic phases are neutralized with 120 ml saturated bicarbonate solution, dried over $Na_2SO_4$ and rotary evaporated. 6.62 g (33 mmol, 98%) 2-(2-nitrophenyl)propyl chloride are obtained as a brown oil.

TLC (silica gel): $R_f$=0.75 (PE/EE 7:3); $^1$H-NMR (250 MHz, $CDCl_3$): 7.80 (dd, 1H, arom. H, o to $NO_2$), 7.60 (m, 1H, arom. H), 7.44 (m, 2H, arom. H), 3.74 (m, 3H, α-$CH_2$, β-CH), 1.46 (d, 3H, $CH_3$); UV (MeOH), λ [nm] (1 g ε): 206 (3.79) [217 (4.05)], 251 (3.60); Elemental analysis: $C_9H_{10}ClNO_2$ (199.6 g/mol)

|       | C     | H    | N    |
|-------|-------|------|------|
| calc. | 54.15 | 5.05 | 7.02 |
| found | 54.24 | 5.01 | 7.06 |

Production of the Phenylalkylsulfonyl Chlorides

Example 6

2-(2-nitrophenyl)ethylsulfonyl chloride 3.7 g 2-(2-nitrophenyl)ethyl chloride (20 mmol) are dissolved with 7.8 g sodium thiosulfate pentahydrate (31 mmol) in 95 ml 50% aqueous methanol and heated 16 h under reflux. The solution is filtered after cooling and rotary evaporated until a precipitate comes down. This is decanted into a 500 ml three-neck flask, cooled to 10° C. and mixed with 100 g ice. A strong chlorine stream is delivered into the solution for 10 Min. Thereby, the temperature should not increase above 10° C. This is stirred a further ½ h at room temperature, such that excess chlorine can escape. The precipitate is drawn off over a Glass filter and dried in a desiccator. For purification, the precipitate is dissolved in chloroform and precipitated with a little petroleum ether. 3.2 g (13 mmol, 65%) 2-(2-nitrophenyl)ethylsulfonyl chloride are obtained as beige crystals.

TLC (silica gel): $R_f$=0.65 (PE/EE 7:3) MP.: 76 to 77° C. (Lit.: 74 to 75° C.) $^1$H-NMR (250 MHz, $CDCl_3$): 8.09 (dd. 1H. arom. H. o to $NO_2$). 7.69 (t, 1H, arom. H), 7.55 (m, 2H, arom. H), 4.10 (t, 2H, α-$CH_2$), 3.62 (t, 2H, β-$CH_2$); UV (MeOH), λ [nm] (1 g ε): 203 (4.00), 214 (3.75), 257 (3.62).

Example 7

2-(2-chloro-6-nitrophenyl)ethylsulfonyl chloride 1.3 g 2-(2-chloro-6-nitrophenyl)ethyl chloride (6 mmol) and 3.7 g sodium thiosulfate pentahydrate (15 mmol) are heated in 50 ml ethanol/water (1:1) for 3 days under reflux. The reaction solution is filtered hot and rotary evaporated until dry. The residue is dissolved in $H_2O$ and extracted 2× with $CH_2Cl_2$, in order to remove non-reacted educt. Chlorine is delivered into the water phase cooled to 3° C. Thereby, attention must be paid to not increase the temperature over 10° C. This is stirred a further 30 Min. so that excess chlorine can escape. The precipitate is drawn off (occurs extremely poorly because this is a viscous, sticky mass). For purification over flash chromatography, the crude product is applied to the column dissolved in a little $CH_2Cl_2$, because it does not completely dissolve in petroleum ether (36 g silica gel, 3×10 cm, Sol.: PE/EE, cond. 9:1, gradient: 200 ml PE/EE 9:1, 80 ml 7:1, 140 ml 6:1, 120 ml 5:1, 100 ml 4:1). 400 mg (1.5 mmol, 25%) 2-(2-chloro-6-nitrophenyl)ethylsulfonyl chloride are obtained as a yellowish solid.

TLC (silica gel): $R_f$=0.19 (PE/EE 9:1); MP.: 75 to 76° C.; $^1$H-NMR (250 MHz, $CDCl_3$): 7.88 (dd, 1H, arom. H), 7.74 (dd, 1H, arom. H), 7.51 (t, 1H, arom. H, m to $NO_2$), 4.08 (t, 2H, α-$CH_2$), 3.63 (t, 2H, β-$CH_2$); UV (MeOH), λ [nm] (1 g ε): 210 (4.23), 255 (3.61), 269 (3.44). Elemental analysis: $C_8H_7Cl_2NO_4S$ (268.1 g/mol)

|       | C     | H    | N    |
|-------|-------|------|------|
| calc. | 33.82 | 2.48 | 4.93 |
| found | 34.11 | 2.50 | 5.10 |

Example 8

2-(4-chloro-2-nitrophenyl)ethylsulfonyl chloride 5.02 g 2-(4-chloro-2-nitrophenyl)ethyl chloride (22 mmol) and 8.89 g sodium thiosulfate pentahydrate (36 mmol) are dissolved in 80 ml 50% aqueous methanol and heated 15 h under reflux. After cooling, this is filtered and the solution is rotary evaporated to 50 ml. This is decanted into a 500 ml three-neck flask and cooled to 10° C. and mixed with 25 ml glacial acetic acid and 100 g ice. After 10 Min. supply of chlorine gas (the temperature should not increase over 10° C.), this is stirred for a further ½ h at room temperature in order to allow excess chlorine to escape. The resulting viscous, sticky precipitate is drawn off, washed with a lot of water and dried overnight over NaOH in a desiccator. The remaining substance in the flask is dissolved in $CH_2Cl_2$, dried over $Na_2SO_4$ and rotary evaporated. The dried precipitate is also taken up $CH_2Cl_2$, combined with the other precipitate and rotary evaporated. The crude product (5.636 g) is applied to silica gel and purified over flash chromatography (150 g silica gel, 5×11 cm, Sol.: PE/EE, cond. 15:1, gradient: 250 ml 15:1, 330 ml 10:1, 340 ml 7.5:1, 360 ml 5:1). 3.38 g (12 mmoL, 55%) 2-(4-chloro-2-nitrophenyl)ethylsulfonyl chloride are obtained as a yellow solid.

TLS (silica qel): $R_f$=0.65 (PE/EE 7:3); MP.: 59 to 61° C.; $^1$H-NMR (250 MHz, $CDCl_3$): 8.11 (d, 1H, $H_a$), 7.63 (dd, 1H, $H_b$), 7.46 (d, 1H, $H_c$), 4.07 (t, 2H, α-$CH_2$), 3.59 (t, 2H, β-$CH_2$); UV (MeOH), λ [nm] (1 g ε): 214 (4.26), 255 (3.60), 300 (3.11). Elemental analysis: $C_8H_7Cl_2NO_4S$ (284.1 g/mol)

|       | C     | H    | N    |
|-------|-------|------|------|
| calc. | 33.82 | 2.48 | 4.93 |
| found | 34.25 | 2.47 | 4.97 |

Example 9

2-(2,4-dinitrophenyl)ethylsulfonyl chloride 9.22 g 2-(2,4-dinitrophenyl)ethyl chloride (40 mmol) and 14.89 g sodium thiosulfate pentahydrate (60 mmol) are dissolved in 180 ml 50% aqueous methanol and heated 16 h under reflux. After cooling, this is filtered and the solution is rotary evaporated to half the volume. This is decanted into a 500 ml Three-neck flask, cooled to 10° C. and the solution is mixed with 50 ml glacial acetic acid and 150 g ice. After 10 Min. supply of chlorine gas (the temperature should not increase over 10° C.), this is stirred a further ½ h at room temperature in order to allow excess chlorine to escape. The resulting viscous, sticky precipitate is drawn off and washed with a lot of water. As with the drawn-off precipitate, the remaining substance in the flask is taken up in $CH_2Cl_2$, dried over $Na_2SO_4$ and rotary evaporated. 7.34 g brown oil (25 mmol, 62%) are obtained which is still impure. For further purification, the respective halves of the crude product are applied to silica gel and purified over flash chromatography (70 g silica gel, 4×11 cm, Sol.: PE/EE, cond.: 15:1, gradient: 200 ml 15:1, 330 ml 10:1, 340 ml 7.5:1, 350 ml 6:1, 360 ml 5:1). A total of 4.37 g (15 mmol, 37%) 2-(2,4-dinitrophenyl)-ethylsulfonyl chloride are obtained as a yellow solid.

TLC (silica gel): $R_f$=0.42 (PE/EE 7:3); MP.: 79 to 80° C. $^1$H-NMR (250 MHz, $CDCl_3$): 8.96 (d, 1H, $H_a$), 8.50 (dd, 1H, $H_b$), 7.78 (d, 1H, $H_c$), 4.12; (t, 2H, α-$CH_2$), 3.73 (t, 2H, β-$CH_2$).; UV (MeOH), λ [nm] (1 g ε): 239 (4.21), [255 (4.12)]; Elemental analysis: $C_8H_7ClN_2O_6S$ (294.7 g/mol)

|       | C     | H    | N    |
|-------|-------|------|------|
| calc. | 32.61 | 2.39 | 9.51 |
| found | 32.80 | 2.31 | 9.15 |

Example 10

2-(2-nitrophenyl)propylsulfonyl chloride 2 g 2-(2-nitrophenyl)propyl chloride (10 mmol) and 3.75 g sodium thiosulfate pentahydrate (15 mmol) are dissolved in 50 ml 50% aqueous methanol and heated 15 h under reflux. After cooling, this is filtered and the solution is rotary evaporated to oil. The oil is decanted into a 250 ml Three-neck flask, cooled to 10° C., mixed with 50 ml $H_2O$, 25 ml glacial acetic acid and 50 g ice. After 10 Min. supply of chlorine gas (the temperature should not increase over 10° C.), this is stirred a further ½ h at room temperature in order to allow excess chlorine to escape. The reaction solution is extracted 1× with 200 ml and 2× each with 75 ml ether. The combined ether phases are washed with 100 ml 5% sodium bisulfite solution and $H_2O$ each, dried over $Na_2SO_4$ and rotary evaporated. The crude product (1.03 9) is applied to silica gel and purified over flash chromatography (34 g silica gel, 3×10 cm, Sol.: PE/EE, cond. 15:1, gradient: 250 ml 15:1, 165 ml 10:1, 170 ml 7.5:1, 180 ml 5:1). 458 mg educt 2-(2-nitrophenyl)propyl chloride and 423 mg (1.6 mmol, 16%) 2-(2-nitrophenyl)-propylsulfonyl chloride are obtained as a reddish oil.

TLC (silica gel) $R_f$=0.51 (PE/EE 7:3); $^1$H-NMR (250 MHz, $CDCl_3$): 7.91 (dd, 1H, arom. H, o to $NO_2$), 7.74 (m, 1H, arom. H), 7.47 (m, 2H, arom. H), 4.19 (m, 2H, α-$CH_2$), 3.96 (m, 1H, β-CH), 1.63 (d, 3H, $CH_3$); UV (MeOH), λ [nm] (1 g ε): 204 (4.15), [216 (3.94)], 252 (3.64); Elemental analysis: $C_9H_{10}Cl_2NO_4S$ (263.7 g/mol)

|       | C     | H    | N    |
|-------|-------|------|------|
| calc. | 40.99 | 3.82 | 5.31 |
| found | 41.40 | 3.77 | 5.08 |

Production of the Nucleoside Derivatives

Example 11

$N^6$-NPEOC-5'-O-[2-(2-nitrophenyl)ethylsulfonyl]-2'-deoxyadenosine

At −45° C. 304 mg 2-(2-nitrophenyl)ethylsulfonyl chloride (1.2 mmol) in 3.5 ml abs. $CH_2Cl_2$ are added drop-wise within 20 Min. to 438 mg $N^6$-NPEOC-2'-deoxyadenosine (1 mmol, co-evaporated 3× each with 4 ml abs. pyridine) in 3.5 ml abs. pyridine. After stirring 4 h at −40 to −20° C., the temperature is increased 2 h to −15 to −5° C. and then allowed to increase a further 1½ h until 0° C. are obtained. After a total of 7½ h, the solution is mixed with 15 ml $H_2O$ and 15 ml $CH_2Cl_2$. The $H_2O$ phase is extracted 2× each with 20 ml $CH_2Cl_2$ and the combined organic phases are dried over $Na_2SO_4$. This is filtered, rotary evaporated and co-evaporated 3× with toluene and 1× with MeOH. The obtained crude product is purified by flash chromatography (37 g silica gel, 4×10 cm, Sol.: $CH_2Cl_2$/MeOH, cond.: 100:1, gradient: 80 ml 100:1, each 100 ml 100:2, 100:3, 100:4 and 100:5). 174 mg (0.2 mmol, 20%) $N^6$-NPEOC-3′,5′-di-O-[2-(2-nitrophenyl)ethylsulfonyl]-2′-deoxyadenosine and 219 mg (0.35 mmol, 35%) $N^6$-NPEOC-5′-O-[2-(2-nitrophenyl)-ethylsulfonyl]-2′-deoxyadenosine are obtained as colorless foams.

TLC (silica gel): $R_f$=0.33 (Tol/EE/MeOH 5:4:1); $^1$H-NMR (250 MHz, $D_6$-DMSO): 10.57 (s, 1H, NH), 8.59 (2× s, 2H, H-C(8), H-C(2)), 8.15 (d, 2H, arom. H NPEOC, o to $NO_2$), 7.96 (d, 1H, arom. H NPES, o to $NO_2$), 7.61 (d, 2H, arom. H NPEOC, m to $NO_2$), 7.47 (m, 3H, arom. H NPES), 6.48 (t, 1H, H-C(1′)), 5.62 (d, 1H, OH-C(3′)), 4.44 (m, 5H, H-C(3′), 2× α-$CH_2$ NPE), 4.10 (m, 1H, H-C(4′)), 3.62 (m, 2H, H-C(5′)), 3.14 (m, 4H, 2× β-$CH_2$ NPE), 2.87 (m, 1H, H-C(2′)), 2.38 (m, 1H, H-C(2′)) UV (MeOH), λ [nm] (1 g ε): 206 (4.56), 266 (4.46), 274 [(4.39)].

Elemental analysis: $C_{27}H_{27}N_7O_{11}S×½ H_2O$ (666.6 g/mol)

|  | C | H | N |
|---|---|---|---|
| calc. | 48.64 | 4.23 | 14.71 |
| found | 48.63 | 4.11 | 14.31 |

Example 12

5′-O-[2-(2-chloro-6-nitrophenyl)ethylsulfonyl]-$N^6$-NPEOC-2′-deoxyadenosine

At −45° C., 290 mg 2-(2-chloro-6-nitrophenyl)ethylsulfonyl chloride (1.02 mmol) in 4 ml abs. $CH_2Cl_2$ are added drop-wise within 20 Min. to 355 mg $N^6$-NPEOC-2′-deoxyadenosine (0.8 mmol, co-evaporated 3× each with 4 ml abs. pyridine) in 4 ml abs. pyridine. After stirring 4 h at −40 to −30° C., the temperature is allowed to increase 2½ h until 0° C. are obtained. After a total of 6½ h, the solution is mixed with 15 ml $H_2O$ and 15 ml $CH_2Cl_2$ and the $H_2O$ phase is extracted 3× each with 15 ml $CH_2Cl_2$. The combined organic phases are dried over $Na_2SO_4$, filtered, rotary evaporated and co-evaporated 3× with toluene and 1× with MeOH. The obtained crude product is purified by flash chromatography (32 g silica gel, 3×10 cm, Sol.: $CH_2Cl_2$/MeOH, cond.: 100:1, gradient: 100 ml 100:1, each 100 ml 100:2, 100:3, 100:4 and 100:5). 214 mg (0.3 mmol, 39%) 5′-O-[2-(2-chloro-6-nitrophenyl)-ethylsulfonyl]-$N^6$-NPEOC-2′-deoxyadenosine are obtained as a colorless foam.

TLC (silica gel): $R_f$=0.36 (Tol/EE/MeOH 5:4:1); $^1$H-NMR (250 MHz, $D_6$-DMSO): 10.56 (s, 1H, NH), 8.58 (s, 2H, H-C(8), H-C(2)) 8.15 (d, 2H, arom. H NPEOC, o to $NO_2$), 7.94 (d, 1H, arom. H NPES), 7.81 (d, 1H, arom. H NPES), 7.56 (d, 3H, 2 arom. H NPEOC, m to $NO_2$, 1 arom. H NPES, m to $NO_2$), 6.47 (t, 1H, H-C(1′)), 5.62 (d, 1H, OH-C(3′)), 4.46 (m, 5H, H-C(3′)), 2×α-$CH_2$ NPE), 4.12 (m, 1H, H-C(4′)), 3.52 (m, 2H, H-C(5′)), 3.21 (m, 2H, β-$CH_2$ NPE), 3.10 (m, 2H, β-$CH_2$ NPE), 2.88 (m, 1H, H-C(2′)), 2.38 (m, 1H, H-C(2′)); UV (MeOH), λ[nm] (1 g ε): 210 (4.62), 266 (4.43), [272 (4.39)];

Elemental analysis: $C_{27}H_{26}ClN_7O_{11}S×½ H_2O$ (701.1 g/mol)

|  | C | H | N |
|---|---|---|---|
| calc. | 46.25 | 3.74 | 13.98 |
| found | 46.33 | 3.79 | 13.48 |

Example 13

5′-O-[2-(4-chloro-2-nitrophenyl)ethylsulfonyl]-$N^4$-PEOC-2′-deoxycytidine

At 0° C., 253 mg 2-(4-chloro-2-nitrophenyl)ethylsulfonyl chloride (0.89 mmol) in 2.5 ml abs. $CH_2Cl_2$ are added drop-wise within 45 Min. to 250 mg $N^4$-NPEOC-2′-deoxycytidine (0.59 mmol, co-evaporated 3× each with 4 ml abs. pyridine) in 2.5 ml abs. pyridine. After stirring 3¾ h at 0° C., the solution is mixed with 10 ml $H_2O$ and 15 ml $CH_2Cl_2$. The $H_2O$ phase is extracted 1× with 15 ml $CH_2Cl_2$. The combined organic phases are dried over $Na_2SO_4$, filtered, rotary evaporated and co-evaporated 3× with toluene and 2× with MeOH. The obtained crude product (942 mg) is purified by flash chromatography (37 g silica gel), 3×10 cm, Sol.: $CH_2Cl_2$/MeOH, cond.: $CH_2Cl_2$, gradient: 100 ml $CH_2Cl_2$, each 200 ml 100:1, 100:2, 100:3 and 100 ml 100:4). 214 mg (0.32 mmol, 34%) 5′-O-[2-(4-chloro-2-nitrophenyl)ethylsulfonyl]-$N^4$-NPEOC-2′-deoxycytidine are obtained as a colorless foam. The obtained mixed fractions are chromatographed once again (5 g silica gel, 1×12 cm, Sol.: $CH_2Cl_2$/MeOH, cond.: $CH_2Cl_2$, gradient: 70 ml $CH_2Cl_2$, each 100 ml 100:5, 100:1 and 50 ml 100:2). 147 ml (0.16 mmol, 27%) 3′-O-[2-(4-chloro-2-nitrophenyl)ethyl-sulfonyl]-$N^4$-NPEOC-2′-deoxycytidine and 24 mg (0.04 mmol, 6%) 3′,5′-Di-O-[2-(4-chloro-2-nitrophenyl)ethylsulfonyl]-$N^4$-NPEOC-2′-deoxycytidine are also obtained as colorless foams.

TLC (silica gel): $R_f$=0.43 (Tol/EE/MeOH 5:4:1); $^1$H-NMR (250 MHz, $D^6$-DMSO): 10.78 (s, 1H, NH), 8.15 (d, 2H, arom. H NPEOC, o to $NO_2$), 8.08 (d, 1H, $H_a$), 8.01 (d, 1H, H-C(6)), 7.75 (dd, 1H, $H_b$), 7.59 (d, 3H, 2 arom. H NPEOC, m to $NO_2$, $H_c$), 6.94 (d, 1H, H-C(5)), 6.14 (t, 1H, H-C(1′)), 5.52 (d, 1H, OH-C(3′) 4.43 (d, 2H, α-$CH_2$ NPE), 4.34 (t, 2H, α-$CH_2$ NPE), 4.21 (m, 1H, H-C(3′)), 4.03 (m, 1H, H-C(4′)), 3.73 (m, 2H, H-C(5′)), 3.25 (m, 2H, β-$CH_2$ NPE), 3.07 (m, 2H, β-$CH_2$ NPE), 2.27 (m, 1H, H-C(2′)), 2.12 (m, 1H, H-C(2′)).

UV (MeOH), λ [nm] (1 g ε): [207 (4.61)], 212 (4.65), 244 (4.36), [269 (4.28)]; Elemental analysis: $C_{26}H_{26}ClN_5O_{12}S$ (668.0 g/mol)

|  | C | H | N |
|---|---|---|---|
| calc. | 46.75 | 3.92 | 10.48 |
| found | 46.82 | 3.97 | 10.16 |

Example 14

5′-O-[2-(2,4-dinitrophenyl)ethylsulfonyl]-$N^2$-NPEOC-$O^6$-NPE-2′-deoxyguanosine At −50° C., 381 mg 2-(2,4-dinitrophenyl)ethylsulfonyl chloride (1.3 mmol) in 3 ml abs. $CH_2Cl_2$ are added drop-wise within 40 Min. to 391 mg $N^2$-NPEOC-$O^6$-NPE-2'-deoxyguanosine (0.65 mmol, co-evaporated 3× each with 8 ml abs. pyridine) in 3 ml abs. pyridine. After stirring 4 h at −50 to −30° C. and 2½ h at −30 to −15° C., the solution is mixed with 15 ml $H_2O$ and 15 ml $CH_2Cl_2$. The $H_2O$ phase is extracted 1× with 20 ml $CH_2Cl_2$ and the combined organic phases are dried over $Na_2SO_4$. This is filtered, rotary evaporated and co-evaporated 3× with toluene and 1× with MeOH. The obtained crude product (730 mg) is purified by flash chromatography (33 g silica gel, 3×9 cm, Sol.: $CH_2Cl_2$/MeOH, cond. $CH_2Cl_2$, gradient: 100 ml $CH_2Cl_2$, each 200 ml 100:0,7, 100:1.4, 100:2, 100:3 and 100:4). 141 mg (0.12 mmol, 19%) slightly impure 3',5'-Di-O-[2-(2,4-dinitrophenyl)ethyl-sulfonyl]-$N^2$-NPEOC-$O^6$-NPE-2'-deoxyguanosine and 339 mg (0.39 mmol, 60%) 5'-O-[2-(2,4-dinitrophenyl)ethylsulfonyl]-$N^2$-NPEOC-$O^6$-NPE-2'-deoxyguanosine are obtained as light yellowish foams.

TLC (silica gel): $R_f$=0.46 (Tol/EE/MeOH 5:4:1); $^1$H-NMR (250 MHz, D6-DMSO): 10.31 (s, 1H, NH), 8.64 (d, 1H, $H_a$), 8.34 (dd, 1H, $H_b$) 8.29 (s, 1H, H-C(8)), 8.15 (d, 4H, arom. H NPE, o to $NO_2$), 7.62 (d, 4H, arom. H NPE, m to $NO_2$) 7.57 (s, 1H, $H_c$), 6.33 (t, 1H, H-C(1')), 5.53 (d, 1H, OH-C(3')), 4.68 (t, 2H, α-$CH_2$ NPE), 4.48 (m, 3H, α-$CH_2$ NPE, H-C(3')), 4.33 (t, 2H, α-$CH_2$ NPE), 4.06 (m, 1H, H-C(4')), 3.66 (m, 2H, H-C(5')), 3.24 (m, 4H, 2×β-$CH_2$ NPE), 3.08 (t, 2H, β-$CH_2$ NPE), 2.89, (m, 1H, H-C(2')), 2.26 (m, 1H, H-C(2')); UV (MeOH), λ [nm] (1 g ε): [206 (4.70)], 214 (4.74), [254 (4.60)], 265 (4.63); Elemental analysis: $C_{35}H_{33}N_9O_{16}S×½ H_2O$ (876.8 g/mol)

|       | C     | H    | N     |
|-------|-------|------|-------|
| calc. | 47.94 | 3.79 | 14.37 |
| found | 48.27 | 3.65 | 14.00 |

Example 15

5'-O-[2-(2-nitrophenyl)propylsulfonyl]-thymidine 242 mg thymidine (1 mmol, co-evaporated 3× each with 5 ml abs. pyridine) are dissolved in 2.5 ml abs. pyridine and cooled to −60° C. 396 mg 2-(2-nitrophenyl)propylsulfonyl chloride (1.5 mmol) in 2.5 ml abs. $CH_2Cl_2$ are added drop-wise to this within 10 Min. After stirring 4 h at a temperature between −60 and −30° C., the temperature is allowed to increase to −15° C. After a total of 6¼ h, the reaction is mixed with 15 ml $H_2O$ and $CH_2Cl_2$ respectively and the aqueous phase is extracted 4× each with 15 ml $CH_2Cl_2$. The combined organic phases are dried over $Na_2SO_4$, filtered and rotary evaporated. This is co-evaporated 3× with toluene and 1× with methanol. The crude product (600 mg) is purified over flash chromatography (39 g silica gel, 3×11 cm, Sol.: $CH_2Cl_2$/MeOH, cond.: $CH_2Cl_2$, gradient: 100 ml $CH_2Cl_2$, each 150 ml 100:1, 100:2, 100:3 and 100:4). 290 mg (0.62 mmol, 62%) 5'-O-[2-(2-nitrophenyl)propyl-sulfonyl]-thymidine are obtained as a colorless foam. The obtained mixed fractions are purified by a further column (4.5 g silica gel, 1×11 cm, Sol.: CH2Cl2/MeOH, cond.: $CH_2Cl_2$, gradient: 100 ml $CH_2Cl_2$, each 50 ml 100:0.5, 100:1 and 100:2). 128 mg (0.18 mmol, 18%) 3',5'-Di-O-[2-(2-nitrophenyl)-propylsulfonyl]-thymidine are isolated as a colorless foam and 26 mg (0.06 mmol, 6%) $^3$'-O-[$^2$-(2-nitrophenyl)-propylsulfonyl]-thymidine as a light red foam.

TLC (silica gel): $R_f$=0.39 (Tol/EE/MeOH 5:4:1); $^1$H-NMR (250 MHz, $D_6$-DMSO): 11.32 (d, 1H, NH), 7.84 to 7.64 (m, 3H, arom. H NPPS), 7.44, (m, 2H, 1 arom. H NPPS, H-C(6)), 6.16 (q, 1H, H-C(1')), 5.45 (q, 1H, OH-C(3')), 4.32 to 4.19 (m, 2H, H-C(5')), 4.06, (m, 1H, H-C(3')), 3.84 (d, 3H, α-$CH_2$ NPPS, H-C(4')), 3.71, (m, 1H, β-CH NPPS), 2.09 (m, 2H, H-C(2')), 1.73 (s, 3H, $CH_3$, thymidine), 1.38 (dd, 3H, $CH_3$ NPPS); UV (MeOH), λ [nm] (1 g ε): 205 (4.28), [217 (4.08)], 262 (4.07); Elemental analysis (Mol. wt.): $C_{19}H_{23}N_3O_9S$ (469.5 g/mol)

|       | C     | H    | N    |
|-------|-------|------|------|
| calc. | 48.61 | 4.94 | 8.95 |
| found | 48.69 | 4.95 | 8.71 |

Irradiation Experiments

1. Implementation

The corresponding protected nucleoside derivatives were irradiated with the aid of an apparatus which consisted of a Hg-ultrahigh pressure lamp (200 W), a IR filter (water), a shutter (automatic shutter for exact regulation of the irradiation time), a standard interference filter (filter 1) with a narrow range around the wavelength 365 nm, a collection lens as well as a cuvette holder thermostatically controlled to ca. 17° C. In order to prevent the overheating of filter 1, a broad spectrum filter UG1 (filter 2) was optionally installed between the shutter and filter 1. In the irradiation experiments, light of the wavelength 365 nm was used such that only the protection groups are excited and not the heterocyclic based. The irradiation occurred in quartz cuvettes (3.5 ml) with 3 ml solution each (starting concentration 0.1 and/or 0.025 mmol/l). After complete irradiation, two samples were taken from the cuvettes and analyzed with the aid of an HPLC system.

The HPLC system from Merck-Hitachi consisted of the following equipment: pump L-7100, auto-sampler L-7200, UV/VIS-dectector (detection wavelength 260 nm) L-7420 and interface D-7000. A LICHROSORB RP 18 from Merck was used as a column. Automatic control occurred with a Compaq computer via the HSM manager.

The following gradient was used for chromatography (solvent: water and acetonitrile) (s. Table 1).

TABLE 1

| Time [min] | $H_2O$ | gradient $H_2O/MeCN$ (1:1) [%] | MeCN [%] | Flow |
|---|---|---|---|---|
| 0 | 100 | 0 | 0 | 1 |
| 3 | 100 | 0 | 0 | 1 |
| 10 | 0 | 100 | 0 | 1 |
| 25 | 0 | 0 | 100 | 1 |
| 30 | 0 | 100 | 0 | 1 |
| 33 | 100 | 0 | 0 | 1 |
| 38 | 100 | 0 | 0 | 1 |

The decrease in the educt (5'-O-protected nucleoside) and the increase in the product (5'-O-deprotected nucleoside) can be followed in the obtained chromatograms. Thereby, the analysis occurred over the area of the individual peaks. The solution of the nucleoside to be irradiated was injected at time point 0 Min. (i.e. before irradiation) as a reference and the area of the obtained peaks was seen as 100% educt. The product was equally processed: the peak area of a 0.1 and/or 0.025 mmolar solution was determined and set as 100%. These reference values were applied to the respective areas of the products and educts from the other time points.

The following values were read from the curves obtained in this manner (conc. in % plotted against time): $t_H$: half-life: the time point, at which half of the educt was reacted conc. $t_H$: concentration of the product at the half-life conc. $t_{end}$: concentration of the product at the last time point examined. This time point was mostly set such that the educt was no longer detectable.

The results of the irradiation experiments are summarized in Table 2.

As gathered from Table 2, the half-lives varied relatively strongly for the various nucleosides. Whereas the 5'-O-phenylpropylsulfonyl-thymidine derivative (Example 15) has the shortest half-life with 49 sec., this is 42 minutes for 5'-O-[2-(2-chloro-6-nitrophenyl)ethylsulfonyl]-protected 2'-deoxyadenosine (Example 12).

As far as the yields of the deprotected nucleosides are concerned, it can be recognized from Table 2 that 5'-O-[2-(2-chloro-6-nitrophenyl)ethylsulfonyl]-protected-2'-deoxyadenosine (Example 11) has the highest with 97%, whereas with the other nucleoside derivatives take on values between ca. 50 and 85%.

TABLE 2

Irradiation of the 5'-O-protected nucleosides

| | | | yield of nucleosides | | |
| --- | --- | --- | --- | --- | --- |
| Example | Compound | $t_H$ | conc. $t_H$ | conc. $t_{end}$ | ($t_{end}$, conc. Educt) |
| 11 | N6-NPEOC-5'-O-[2-(2-nitrophenyl)ethylsulfonyl]-2'-deoxyadenosine[1] | 21 Min. | 49% | 97% | (120 Min, 3%) |
| 12 | 5'-O-[2-(2-chloro-6-nitrophenyl)ethylsulfonyl]-N6-NPEOC-2'-of deoxyadenosine[1] | 42 Min. | 38% | 68% | (120 Min, 16%) |
| 13 | 5'-O-[2-(4-chloro-2-nitrophenyl)ethylsulfonyl]-N4-NPEOC-2'-deoxycytidine[1] | 15.8 Min | 32% | 71% | (120 Min, 1%) |
| 14 | 5'-O-[2-(2,4-dinitrophenyl)ethylsulfonyl]-N2-NPEOC-O6-NPE-2'-deoxyguanosine[2] | 16.3 Min | 40% | 85% | (120 Min, 0%) |
| 15 | 5'-O-[-(2-nitrophenyl)propylsulfonyl]-thymidine[1] | 49 sec. | 26% | 48% | (600 sec., 0%) |

[1] concentration: 0.1 mmol/l; solvent: MeOH/H$_2$O 1:1
[2] concentration: 0.025 mmol/l; solvent: MeOH/H$_2$O 3:2

What is claimed is:

1. A nucleoside derivative having a photolabile protective group of the general formula (I):

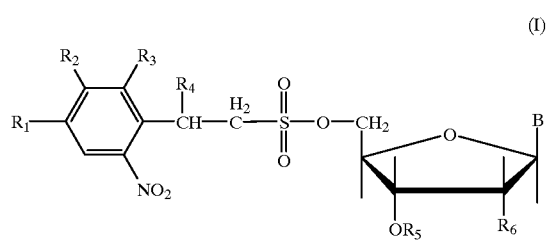

(I)

in which $R_1$=H, NO$_2$, CN, OCH$_3$, halogen or alkyl or alkoxyalkyl having about 1 to about 4 C atoms $R_2$=H, OCH$_3$ $R_3$=H, F, Cl, Br, NO$_2$, or an aliphatic acyl radical with about 2 to about 5 C atoms $R_4$=H, halogen, OCH$_3$, an alkyl radical having about 1 to about 4 C atoms or an optionally substituted aryl radical $R_5$=H or a phosphoramidite group $R_6$=H, OH, halogen or XR$^8$, where X=O, R$^8$ is selected from alkyl, alkenyl, acetal, and silyl ether protective groups; where X=S, R$^8$ is an alkyl protective group, B=9-adeninyl, 1-cytosinyl, 9-guaninyl, 1-thyminyl, 1-uracilyl, 2,6-diaminopurin-9-yl, hypoxanthin-9-yl, 5-methylcytosin-1-yl, 5 amino-4-imidazolcarboxamid-1-yl, and 5-amino-4-imidazolcarboxamid-3-yl, where in the case of B=9-adeninyl, 1-cytosinyl, or 9-guaninyl, the primary amino function is optionally substituted with a permanent protective group.

2. The nucleoside derivatives according to claim 1, wherein in the case of R$^4$≠H, R$^1$=R$^2$=R$^3$=H.

3. The nucleoside derivatives according to claim 1, wherein R$^4$ represents a methyl radical.

4. The nucleoside derivatives according to claim 1, wherein R$^5$ represents a phosphoramidite group of the formula:

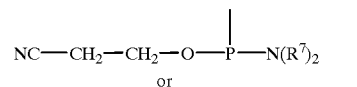

or

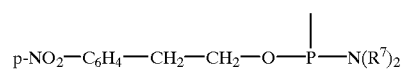

wherein the R$^7$ groups are the same or different and represent linear or branched alkyl radicals having about 1 to about 4 C atoms.

5. The nucleoside derivatives according to claim 4, wherein R$^7$ represents an ethyl or isopropyl radical.

6. The nucleoside derivatives according to claim 1, wherein R$^6$ is an XR$^8$ group and R$^8$ represents an alkyl, alkenyl, acetal or silyl ether protective group in the case of X=O, or an alkyl protective group in the case of X=S.

7. The nucleoside derivative according to claim 6, wherein $R_6$ is a radical selected from the group consisting of O-methyl, O-ethyl, O-allyl, O-tetrahydropyranyl, O-methoxytetrahydropyranyl, and O-t-butyldimethylsilyl.

8. The nucleoside derivative according to claim 1 wherein B is selected from the group consisting of adeninyl, cytosinyl, and guaninyl and the permanent protective group is selected from the group consisting of phenoxyacetyl and dimethylformamidino.

9. The nucleoside derivative according to claim 1 wherein B is adeninyl and the permanent protective group is selected from the group consisting of benzoyl and p-nitrophenylethoxycarbonyl-(p-NPEOC) radicals.

10. The nucleoside derivative according to claim 1 wherein B is guanyl and the permanent protective group is selected from the group consisting of isobutyroyl, p-nitrophenylethyl (p-NPE) and p-nitrophenylethoxycarbonyl-(p-NPEOC) radicals.

11. The nucleoside derivative according to claim 1 wherein B is cytosinyl and the permanent protective group is selected from the group consisting of benzoyl and p-nitrophenylethoxycarbonyl-(p-NPEOC) radicals.

12. The nucleoside derivative according to claim 1 wherein $R^1$ is selected from the group consisting of a fluorine atom, chlorine atom, and bromine atom and $R^6$ is selected from the group consisting of a fluorine atom, chlorine atom, and bromine atom.

13. The method for preparing a nucleoside derivative, said method comprising:

a) reacting thionyl chloride with an alcohol of the general formula:

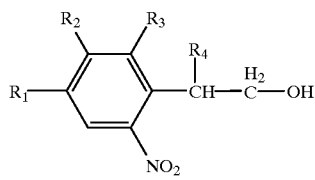

in which:
$R_1$=H, $NO_2$, CN, $OCH_3$, halogen or alkyl or alkoxyalkyl having about 1 to about 4 C atoms
$R_2$=H, $OCH_3$
$R_3$=H, F, Cl, Br, $NO_2$, or an aliphatic acyl radical with about 2 to about 5 C atoms
$R_4$=H, halogen, $OCH_3$, an alkyl radical having about 1 to about 4 C atoms or an optionally substituted aryl radical; to form a phenylalkyl chloride of the formula:

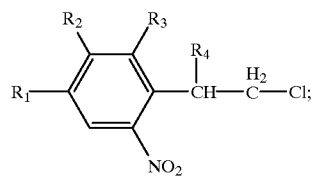

b) contacting the phenylalkyl chloride formed in step a) with sodium thiosulfate and then with chlorine to produce a phenylalkylsulfonyl chloride of the general formula:

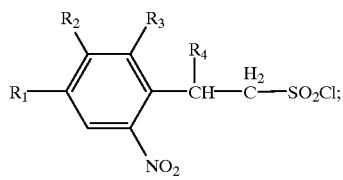

c) reacting the phenylalkylsulfonyl chloride formed in step b) with a nucleoside of the general formula:

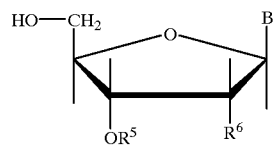

wherein:
$R_5$=H or a phosphoramidite group
$R_6$=H, OH, halogen or $XR^8$, where X=O, $R^8$ is selected from alkyl, alkenyl, acetal, and silyl ether protective groups; where X=S, $R^8$ is an alkyl protective group,
B=9-adeninyl, 1-cytosinyl, 9-guaninyl, 1-thyminyl, 1-uracilyl, 2,6-diaminopurin-9-yl, hypoxanthin-9-yl, 5-methylcytosin-1-yl, 5 amino-4-imidazolcarboxamid-1-yl, and 5-amino-4-imidazolcarboxamid-3-yl, where in the case of B=9-adeninyl, 1-cytosinyl, or 9-guaninyl, the primary amino function optionally exhibits a permanent protective group, thereby producing a nucleoside derivative.

14. The method according to claim 13, wherein step a) is performed in a nonpolar organic solvent at temperatures between about 50 and about 120° C. in the presence of a base.

15. The method according to claim 13, wherein in relation to the alcohol component, a two- to five-fold excess of said thionyl chloride is used in step a).

16. The method according to claim 13 further comprising in step a), using toluene as a nonpolar organic solvent for the reaction of the alcohol with thionyl chloride.

17. The method according to claim 16 further comprising in step a), using pyridine as a base.

18. The method according to claim 17, wherein pyridine is used in an amount of about 2 to about 10 Vol. % with respect to the toluene used.

19. The method according to claim 16, wherein the concentration of said alcohol component is about 1.0 to about 20.0 mmol per 10 ml solvent in step a).

20. The method according to claim 13 further comprising in step b), a solvent mixture comprising an alcohol and water for the reaction with sodium thiosulfate, said reaction with sodium thiosulfate being performed between about 50 and about 100° C.

21. The method according to claim 20, wherein methanol or ethanol is used as an alcohol.

22. The method according to claim 13, wherein 1.5 to about 2.5 mmol sodium thiosulfate is used per mmol phenylalkyl chloride in step b).

23. The method according to claim 13 further comprising in step b), a solvent selected from the group consisting of water, water/acetic acid, and water/dichloromethane, wherein said contacting with chlorine is carried out at between about 0 and about +25° C. in the solvent.

24. The method according to claim 13, further comprising in step c) a solvent mixture comprising dichloromethane and pyridine, wherein the reaction in step c) is carried out in the solvent mixture at a temperature between about −60 and about 0° C.

25. The method according to claim 13, wherein the molar ratio of nucleoside to phenylalkylsulfonyl chloride is about 1:1 to about 1:2.

26. The method according to claim 13 further comprising:
in step c), dissolving the phenylalkylsulfonyl chloride in dichloromethane,
dissolving the nucleoside in pyridine, wherein the nucleoside is charged;
bringing the phenylalkylsulfonyl chloride to a reaction temperature; and
adding the phenylalkylsulfonyl chloride drop-wise to the nucleoside dissolved in pyridine.

27. The method according to claim 24, wherein the concentration of the nucleoside in said solvent mixture in step c) is about 0.1 to about 3.0 mmol per 10 ml solvent.

28. The method of claim 13, wherein in the step of reacting the phenylalkylsulfonyl chloride, $R^5$ is H, and the method further comprises:
d) introducing in the 3' position of said nucleoside derivative a phosphoramidite group selected from the group consisting of:

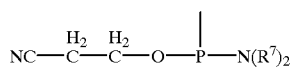

-continued
and

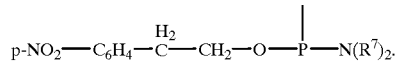

29. The method according to claim 28 further comprising reacting at temperatures between about 0 and about 25° C. said nucleoside derivative with the corresponding phosphine in the presence of 1H-tetrazole as an activator in a solvent mixture comprising dichloromethane and acetonitrile.

30. The method for synthesizing an oligonucleotide comprising the steps of:
a) providing a nucleoside derivative of claim 1 and an oligonucleotide chain comprising at least one nucleotide comprising a reactive group;
b) covalently adding the nucleoside derivative of claim 1 to the oligonucleotide chain;
c) deprotecting the nucleoside derivative according to claim 1, said deprotecting being carried out with light of an appropriate wavelength.

31. The method of claim 30 further comprising:
providing a solid carrier material, wherein the oligonucleotide chain is attached to the solid carrier material.

* * * * *